United States Patent [19]

Michaelian

[11] Patent Number: Plant 5,709

[45] Date of Patent: Apr. 8, 1986

[54] PEACH TREE (RS-2)

[75] Inventor: Albert H. Michaelian, Dinuba, Calif.

[73] Assignee: Richland Sales Co., Reedley, Calif.

[21] Appl. No.: 663,072

[22] Filed: Oct. 19, 1984

[51] Int. Cl.[4] ..... A01H 5/03

[52] U.S. Cl. ..... Plt./43

[58] Field of Search ..... Plt./43

*Primary Examiner*—Robert E. Bagwill

*Attorney, Agent, or Firm*—Roger B. Webster

[57] ABSTRACT

A peach tree which is of medium size, vigorous, upright, dense, round-topped, and hardy; foliated with large, oval-lanceolate, abruptly pointed leaves having a glandular, finely serrate margin, a petiole of medium length and thickness, and medium size, alternate, green, reniform glands; blooms early with medium size, pink flowers whose buds are hardy, free, and of medium size and length; and is a regular and very productive bearer of uniform, medium size, broadly compressed, globose, freestone, early-ripening fruit having yellow skin blushed with red, and yellow flesh.

1 Drawing Figure

BACKGROUND OF THE VARIETY

1. Field of the Invention

In the operation and maintenance of a ranch, located near Dinuba, Tulare County, Calif., I do—as owner—travel about such ranch for the purpose of inspection, soil cultivation, irrigation, and harvesting of crops. Against this background of activities, the present variety of peach tree was discovered by me.

2. Classification of the Variety

The present variety of peach tree is embraced by Class 43, Plants, of the United States Patent Office MANUAL OF CLASSIFICATION.

3. Prior Varieties

Among existing varieties of peach trees which are known to me, and mentioned herein, is the May Crest (U.S. Plant Pat. No. 4,064).

ORIGIN OF THE VARIETY

The present variety of peach tree was discovered by me growing as a sport limb on one tree in a May Crest orchard on my ranch located as aforesaid; it having been observed by me—during the approach of a harvest season—that the fruit on such sport limb matured earlier than the remainder of the fruit on the tree. Subsequently, I maintained such sport limb under close and continued annual observation in order to confirm the early ripening and other characteristics of its fruit. With such confirmation, I determined to asexually reproduce the variety in anticipation of commercial growing thereof.

ASEXUAL REPRODUCTION OF THE VARIETY

The present variety of peach tree was asexually reproduced, on my behalf, by budding undertaken by a commercial nursery, and the reproductions, grown on my said ranch, ran true—in maturity—in all respects.

SUMMARY OF THE VARIETY

The present variety of peach tree is of medium size, vigorous, upright, dense, round-topped, and hardy; foliated with large, oval-lanceolate, abruptly pointed leaves having a glandular, finely serrate margin, a petiole of medium length and thickness, and medium size, alternate, green, reniform glands; blooms early with medium size, pink flowers whose buds are hardy, free, and of medium size and length; and is a regular and very productive bearer of uniform, medium size, broadly compressed, globose, freestone, early-ripening fruit having yellow skin blushed with red, and yellow flesh.

The present variety of peach tree is further and more particularly characterized by fruit which—while generally similar to the May Crest—has a harvest period abour four to five days earlier, and is of larger size, more uniform, and with slightly more red blush.

BRIEF DESCRIPTION OF THE DRAWING

The drawing is an illustration, by photographic reproduction in color, of separate fruit of the present variety; one fruit remaining attached to a twig with leaves, and another fruit being half cut away to expose the flesh and with the stone remaining in place.

DESCRIPTION OF THE VARIETY

The botanical details of this new and distinct variety of peach tree—with color definitions (except those in common color terms) referenced to Maerz and Paul Dictionary of Color—are as follows:

Tree:
- *Size.*—Medium.
- *Vigor.*—Vigorous.
- *Growth.*—Upright.
- *Density.*—Dense.
- *Form.*—Round-topped.
- *Hardiness.*—Hardy.
- *Production.*—Very productive.
- *Bearing.*—Regular bearer.

Trunk:
- *Size.*—Medium.
- *Texture.*—Medium.

Branches:
- *Size.*—Medium.
- *Texture.*—Medium.
- *Color.*—New wood — Green. Mature wood — Brown.

Lenticels:
- *Number.*—Medium.
- *Size.*—Medium.

Leaves:

*Size.*—Large. Average length — $7\frac{1}{2}''$. Average width — $1\frac{3}{4}''$.
*Form.*—Oval — lanceolate. Abruptly pointed.
*Thickness.*—Medium.
*Color.*—Top side — Dark green (23-L-7). Under side — Lighter green (22-J-6).
*Texture.*—Smooth.
*Margin.*—Glandular. Finely serrate.
*Petiole.*—Medium length. Medium thickness.
*Glands.*—Average number — 1 to 2. Alternate. Medium size. Reniform. Green.

Flower buds:
*Hardiness.*—Hardy.
*Size.*—Medium.
*Length.*—Medium.
*Form.*—Free.

Flowers:
*Blooming period.*—Feb. 27, 1984. Early.
*Size.*—Medium.
*Color.*—Pink.

Fruit:
*Maturity when described.*—Hard ripe.
*Date of first picking.*—May 12, 1984.
*Date of last picking.*—May 17, 1984.
*Size.*—Uniform. Medium. Average diameter axially — $2\frac{1}{4}''$. Average transversely in suture plane — $2\frac{3}{4}''$.
*Form.*—Uniform. Globose. Broadly compressed.
*Suture.*—A shallow, inconspicuous line extending from base to beyond but discontinuous at apex, with slight depression beyond pistil point.
*Ventral surface.*—Rounded slightly.
*Lips.*—Equal.
*Cavity.*—Rounded. Circular. Elongated in suture plane with suture showing on both sides. Average depth — $\frac{3}{8}''$. Average breadth — $\frac{3}{4}''$.
*Base.*—Rounded.
*Apex.*—Short.
*Pistil point.*—Apical.

Skin:
*Thickness.*—Medium.
*Texture.*—Medium.
*Tenacity.*—Tenacious to flesh.
*Tendency to crack.*—None in wet season.

*Color.*—Ground color — Yellow (10-L-2) substantially overspread with red (7-L-5). Partially mottled.
*Pubescence.*—Short. Does not roll up when rubbed.

Flesh:
*Color.*—Yellow (11-L-5) with reddish tinge.
*Surface of pit cavity.*—Red with white fibers.
*Amygdalin.*—Moderate.
*Texture.*—Firm. Crisp. Meaty.
*Fibers.*—Fine.
*Ripens.*—Evenly.
*Flavor.*—Mild.
*Aroma.*—Distinct.
*Eating quality.*—Good.

Stone
*Type.*—Free. Parts from flesh smoothly.
*Fibers.*—Short.
*Size.*—Medium. Average length — $1\frac{1}{4}''$. Average breadth — $\frac{3}{4}''$. Average thickness — $\frac{5}{8}''$.
*Form.*—Oblong — Oval.
*Base.*—Oblique.
*Hilum.*—Oval.
*Apex.*—Rounded.
*Sides.*—Equal.
*Surface.*—Regularly furrowed.
*Ridges.*—Rounded.
*Pits.*—Circular.
*Ventral edge.*—Thin.
Dorsal edge.—Shallow.
*Color.*—Beige (11-H-6).
*Tendency to split.*—Slight.

Use: Market.
Keeping quality: Good.
Shipping Quality: Good.
Resistance to insects and diseases: Good.

The peach tree and its fruit herein described may vary in slight detail due to climatic and soil conditions under which the variety may be grown; the present description being of the variety as grown in the Central Valley of California.

We claim:

1. A new and distinct variety of peach tree, substantially as illustrated and described, particularly characterized by fruit which—while generally similar to the May Crest—has a harvest period about four to five days earlier, and is of larger size, more uniform, and with slightly more red blush.

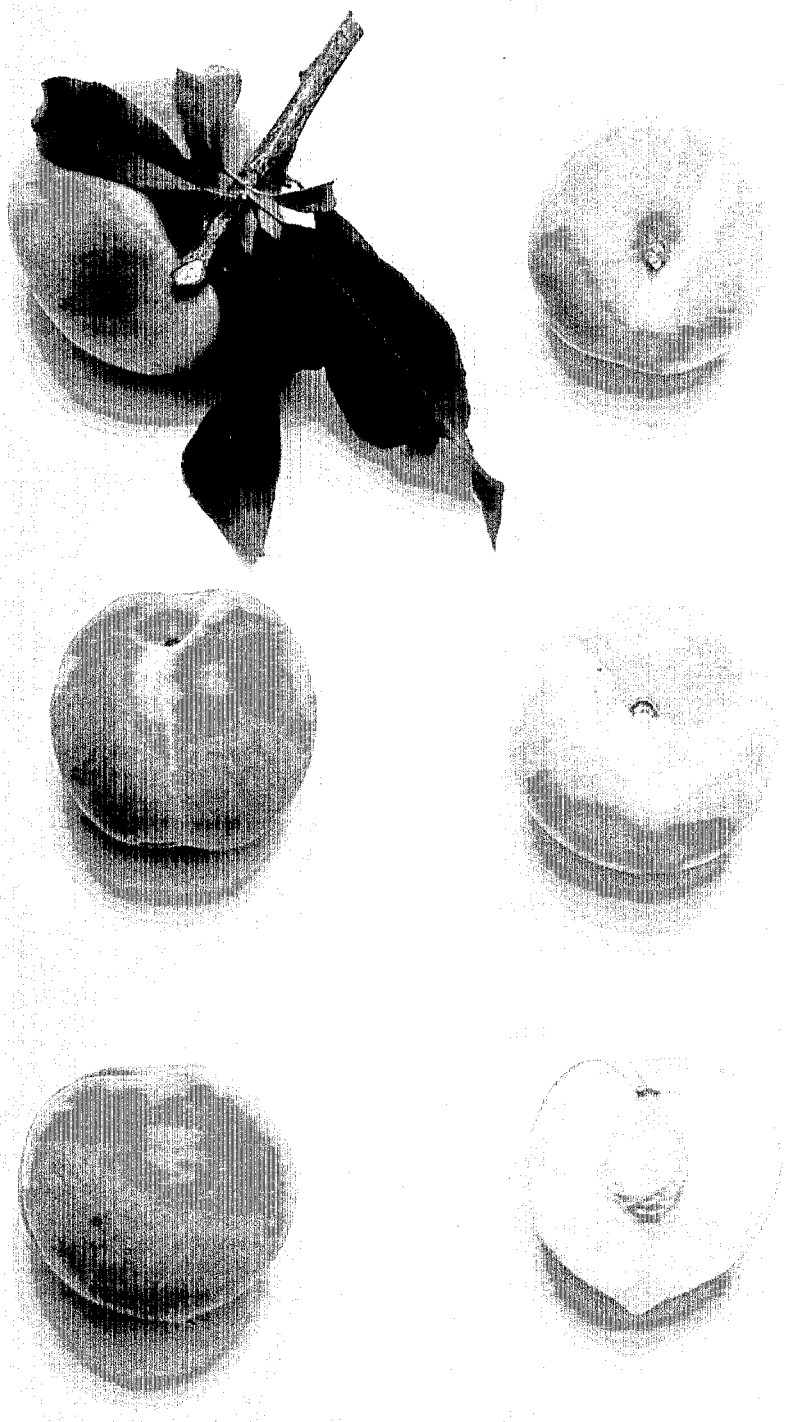

* * * * *